United States Patent [19]

Hermecz et al.

[11] Patent Number: 5,475,000
[45] Date of Patent: Dec. 12, 1995

[54] 3-(SUBSTITUTED TETRAZOLYL)-4-OXO-4H-PYRIDO-[1,2-A]PYRIMIDINES, SALTS THEREOF, PHARMACEUTICAL COMPOSITIONS CONTAINING THEM AND PROCESS FOR PREPARING SAME

[75] Inventors: István Hermecz; József Knoll; Judit Sipos; Klára Gyires; Ágnes Horváth; Lelle Vasvári; László Tardos, all of Budapest; Mária Balogh, Dunakeszi; Zoltán Kapui; Ilona Papp, both of Budapest, all of Hungary

[73] Assignee: Chinoin Gyogyszer-es Vegyeszeti Termekek Gyara Rt., Budapest, Hungary

[21] Appl. No.: 193,080

[22] PCT Filed: Aug. 13, 1992

[86] PCT No.: PCT/HU92/00031

§ 371 Date: Feb. 10, 1994

§ 102(e) Date: Feb. 10, 1994

[87] PCT Pub. No.: WO93/04065

PCT Pub. Date: Mar. 4, 1993

[30] Foreign Application Priority Data

Aug. 13, 1991 [HU] Hungary .................... 6205/90

[51] Int. Cl.[6] .................. C07D 471/04; A61K 31/505
[52] U.S. Cl. .................................... 514/258; 544/282
[58] Field of Search ........................ 514/258; 544/282

[56] References Cited

U.S. PATENT DOCUMENTS

| | | | |
|---|---|---|---|
| 3,055,911 | 9/1962 | Finnegan | 548/250 |
| 4,122,274 | 10/1978 | Juby | 544/282 |
| 4,372,953 | 2/1983 | Uchida | 424/248.5 |
| 4,432,986 | 2/1984 | Erickson | 548/252 |
| 4,457,932 | 7/1984 | Juby | 424/251 |
| 4,474,792 | 10/1984 | Erickson | 424/269 |
| 4,540,703 | 9/1985 | Uchida | 548/251 |
| 4,845,227 | 7/1989 | Hirsch | 548/250 |
| 5,049,572 | 9/1991 | Scherren | 548/252 |
| 5,237,070 | 8/1993 | Scherren | 548/251 |

OTHER PUBLICATIONS

Colton Gastroenterology, vol. 88, No. 5, Part 2, BMY-26517-31, A Mast Cell Stabilizer With Cytoprotective Properties (1985).

Primary Examiner—Mark L. Berch
Attorney, Agent, or Firm—Herbert Dubno; Jonathan Myers

[57] ABSTRACT

4-oxo-4H-pyrido[1,2-a]-pyrimidines are disclosed of the formula

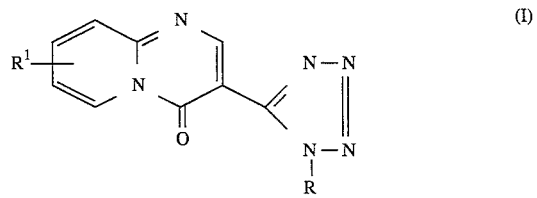

and/or

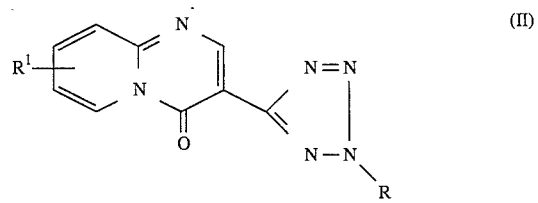

wherein

R is a $C_{1-6}$alkyl, $C_{3-6}$alkenyl, $C_{3-6}$alkynyl, $C_{3-7}$cycloalkyl, $-(CH_2)_n-COOR^3$ wherein $R^3$ is $C_1$ to $C_4$ alkyl and n is 0 or 1 or a $C_{7-8}$ aralkyl group, optionally substituted by one or more halogen atom(s), or by a nitro-group, $R^1$ is a hydrogen atom or a $C_{1-4}$ alkyl group, and salts thereof, as well as a process for their preparation, and pharmaceutical compositions containing them. These compounds are therapeutically useful as gastroprotectives in the treatment and prevention of ulcer.

11 Claims, No Drawings

3-(SUBSTITUTED TETRAZOLYL)-4-OXO-4H-PYRIDO-[1,2-A]PYRIMIDINES, SALTS THEREOF, PHARMACEUTICAL COMPOSITIONS CONTAINING THEM AND PROCESS FOR PREPARING SAME

FIELD OF THE INVENTION

This invention relates to therapeutically useful novel 3-(1-substituted-1H-tetrazol-5-yl)-4-oxo-4H-pyrido[1,2-a]pyrimidines and/or 3-(2-substituted-2H-tetrazol-5-yl)-4-oxo-4H-pyrido[1,2-a]pyrimidines, salts thereof, process for their preparation, and pharmaceutical compositions containing them. These new compounds are therapeutically useful first of all as gastroprotectives in the treatment and prevention of ulcers.

BACKGROUND OF THE INVENTION

It is known that some representatives of the 4H-pyrido[1,2-a]pyrimidine-4-ones exert significant antiallergic and ulcus preventing activity (EP-PS No. 217 673 and 218 423, BE-PS No. 873 192 and 873 194 and U.S. Pat. No. 4,122, 274 and 4,457,932). Cyctoprotective activity of the 9-methyl-3-tetrazolyl- 4-oxo-4H-pyrido[1,2-a]pyrimidine potassium salt was shown more in detail (Gastroenterology 1985 88, 1354).

SUMMARY OF THE INVENTION

The invention is based upon the unexpected discovery that substitution of the acidic hydrogen atom of the tetrazolyl group of the 3-tetrazolyl-4-oxo-4H-pyrido[1,2-a]pyrimidines results in derivatives with a broader therapeutic spectrum.

More particularly the invention relates to novel 4-oxo-4H-pyrido[1,2-a]pyrimidines of the formula

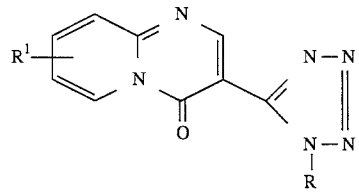

(I)

and/or

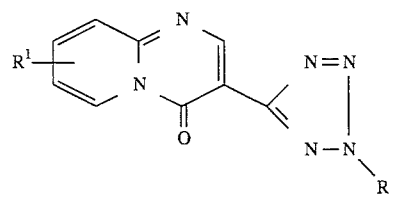

(II)

wherein
R means a $C_{1-6}$alkyl, —$(CH_2)_n$—$COOR^3$ wherein $R^3$ is $C_1$ to $C_4$ alkyl and $C_{3-6}$alkenyl, $C_{3-6}$alkynyl, $C_{3-7}$ cycloalkyl, or a $C_{7-8}$ aralkyl group, optionally substituted by one or more halogen atom(s), or by a nitrogroup, $R^1$ stands for hydrogen atom or a $C_{1-4}$ alkyl group.

As used herein: the term $C_{1-4}$alkyl means straight or branched chain aliphatic saturated hydrocarbyl groups (such as the methyl, n-propyl, isopropyl, n-butyl, isobutyl, tert.-butyl, neopentyl group).

Pharmaceutically acceptable salts of the compounds of the formulae (I) and (II) mean salts formed with alkali metals, alkaline-earth metals, or acid addition salts formed with organic or inorganic acids.

According to another aspect of the invention there is provided a process for the preparation of the new compounds of the formulae (I) and (II), wherein R and $R^1$ are the same as defined above, and their pharmaceutically acceptable salts, which comprises reacting a 3-tetrazolyl-4-oxo-4H-pyrido[1,2-a]pyrimidine of the formula

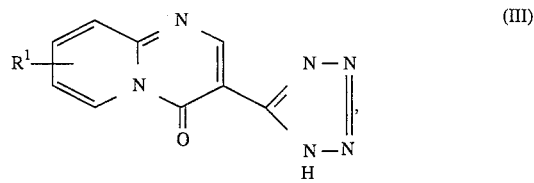

(III)

wherein $R^1$ is the same as defined above, with a halogenide of the formula
wherein R a $C_{1-6}$alkyl, $C_{3-6}$alkenyl, $C_{3-6}$alkynyl, $C_{3-7}$cycloalkyl, or $C_{1-4}$ alkoxycarbonyl group or a $C_{7-8}$aralkyl group optionally substituted by a one ore more halogen atom(s) or by nitro-group and X stands for chlorine, bromine or iodine atom; or with a sulfate of the formula

(V)

wherein R means $C_{1-6}$alkyl, $C_{3-6}$alkenyl, $C_{3-6}$ alkynyl, or $C_{3-7}$cycloalkyl group or a $C_{7-8}$ aralkyl group optionally substituted by one or more halogen atom(s) or by a nitro group or with a sulfonate of the formula

(VI)

wherein R means a $C_{1-6}$alkyl, $C_{3-6}$alkenyl, $C_{3-6}$ alkynyl, or $C_{3-7}$cycloalkyl group or a $C_{7-8}$aralkyl group, optionally substituted by one or more halogen atom(s) or by a nitro group and $R^2$ means a phenyl, p-methylphenyl or methyl group; or with a phosphate of the formula

(VII)

wherein R means a $C_{1-6}$alkyl, $C_{3-6}$alkenyl, $C_{3-8}$ alkynyl, $C_{3-7}$cycloalkyl group or a $C_{7-8}$aralkyl group optionally substituted by one or more halogen atom(s) or by a nitro group; or with an ester of the formula

X—$(CH_2)_n$—$COOR^3$ (VIII), wherein $R^3$ means a $C_{1-4}$alkyl group, X stands for chlorine or bromine atom: and n is 0 or 1, preferably in the presence of a solvent and an acid-binding agent, and if desired separating the thus obtained mixture of the isomers of the formulae (I) and (II) from one-another by using one of the chromatographic methods or by crystallization, utilizing the differences in the solubility of the isomers, and if desired converting the isomers of the formulae (I) and (II) or the mixture thereof into their salts, and if desired liberating them from their salts and converting them to another salt thereof in a known way.

In the preparation process according to the invention compounds of the formula (III) are treated with agents suitable to introduce the R moiety. Thus halogenides of the formula (IV) preferably chlorides, bromides or iodides, or sulfates of the formula (V), sulfonates of general formula (VI), phosphates of the formula (VII) and esters of the formula (VIII) may be applied. Introduction of the R moiety can be accomplished at temperatures ranging between 20°–250° C., preferably in the presence of a solvent. The temperature may be chosen according to the solvent. The reaction may preferably be carried out in the presence of an acid-binding agent; thus alkali hydroxides, preferably sodium hydroxide, potassium hydroxide, or alkaline-earth metal hydroxides, preferably calcium hydroxide, magnesium hydroxide, or alkali carbonates, preferably sodium carbonate, potassium carbonate, potassium hydrogen carbonate may be used. If desired the reaction may be carried out by applying the alkali metal or alkaline-earth metal salts of compounds of the formula (III).

As solvent excess amounts of the compounds of the formulae (IV), (V), (VI) or (VII) may be used, furthermore alcohols (e.g. ethanol, propanol) ketones (e.g. acetone, methyl ethyl ketone), dipolar-aprotic solvents such as dimethylformamide, dimethylsulphoxide, hexamethylphosphortriamide, acetonitrile, nitromethane, aromatic hydrocarbons, (e.g. benzene) or halogenated hydrocarbons (e.g. chlorobenzene; chloroform) and a mixture of the above solvents may be applied. The solvents may contain optional amounts of water.

The starting nitrogen-bridgehead compounds are known materials (U.S. Pat. No. 4,122,274).

Toxicity of the compounds of the the formulae (I) and (II) is low, in general their oral $LD_{50}$ values are higher than 250 mg/kg in rats and mice.

The compounds of the formulae (I) and (II) and their pharmaceutically acceptable salts possess significant gastroprotective effect and exert their protective- and healing (therapeutic) action both in the stomach and in the small intestine. Activity of the compounds of the formulae (I) and (II) was demonstrated in standard tests generally accepted for determining antiulcerogenic effect. Compounds of the formulae (I) and (II) may be used separately or in the form of their isomeric mixture as the active component of pharmaceutical preparations.

As an example, the protective action of the compounds according to the invention against gastric ulcer induced by 0.5 ml of a 1:0.02 volume ratio mixture of 96% ethanol and hydrochloric acid is illustrated in Table 1. [for the method, see: Gastroenterology 77, 433 (1979)]

TABLE 1

Protective action in rats of the compounds according to the invention against the gastric mucosa lesion induced by 96% ethanol containing hydrochloric acid

| Compound $ID_{50}$ p.o. | $ID_{50}$ | |
|---|---|---|
| | mg/kg p.o. | M/kg |
| 3-(1-isopropyl-1H-tetrazol-5-yl)-9-methyl-4-oxo-4H-pyrido[1,2-a]pyrimidine | 0.34 | 1.25 |
| 3-(2-isopropyl-2H-tetrazol-5-yl)-9-methyl-4-oxo-4H-pyrido[1,2-a]- | 0.23 | 0.85 |

TABLE 1-continued

Protective action in rats of the compounds according to the invention against the gastric mucosa lesion induced by 96% ethanol containing hydrochloric acid

| Compound $ID_{50}$ p.o. | $ID_{50}$ | |
|---|---|---|
| | mg/kg p.o. | M/kg |
| pyrimidine | | |
| 3-(2-isopropyl-2H-tetrazol-5-yl)-4-oxo-4H-pyrido[1,2-a]pyrimidine | 2.2 | 8.5 |
| 3-(2-butyl-2H-tetrazol-5-yl)-9-methyl-4-oxo-4H-pyrido[1,2-a]-pyrimidine | 2.0 | 7.0 |
| 3-(allyl-2H-tetrazol-5-yl)-9-methyl-4-oxo-4H-pyrido[1,2-a]pyrimidine | 2.9 | 11.0 |
| 3-(2-propyl-2H-tetrazol-5-yl)-9-methyl-4-oxo-4H-pyrido[1,2-a]-pyrimidine | 0.05 | 0.18 |

The effect of the compounds to the invention, given as examples, against the indomethacin-induced ulcer [Arch. Int. Pharmacodyn 117, 113 (1964)] is shown in Table 2.

TABLE 2

Inhibition of the indomethacin-induced gastric mucosa lesion in rats

| Compound $ID_{50}$ p.o. | $ID_{50}$ | |
|---|---|---|
| | mg/kg p.o. | M/kg |
| 3-(2-isopropyl-2H-tetrazol-5-yl)-9-methyl-4-oxo-4H-pyrido[1,2-a]-pyrimidine | 2.6 | 9.6 |
| 3-(2-allyl-2H-tetrazol-5-yl)-9-methyl-4-oxo-4H-pyrido[1,2-a]-pyrimidine | 2.5 | 9.3 |
| 3-(2-isopropyl-2H-tetrazol-5-yl)-4-oxo-4H-pyrido[1,2-a]pyrimidine | 4.0 | 15.6 |
| 3-(2-propyl-2H-tetrazol-5-yl)-9-methyl-4-oxo-4H-pyrido[1,2-a]-pyrimidine | 5.5 | 20.3 |

To demonstrate the inhibiting effect of the compounds on the formation of indomethacin-induced duodenal ulcer in rat, the effect of 3-(2-propyl-2H-tetrazol-5-yl)-9-methyl-4-oxo- 4H-pyrido[1,2-a]pyrimidine is given as an example.

According to the method of Tsuromi (J. Pharm. Dyn. 1980, 3, 659) the compound was administered to the rats in a dose of 50 mg/kg on 4 consecutive days. On the 2nd day a 15 mg/kg oral dose of indomethacin was given to the rats. The ulcer formation was determined in the small intestine on the 3rd day following the administration of the indomethacin. In comparison to the control, the compound according to the invention exerted an inhibition of 20% on the ulcer formation and also an inhibition of 100% on the lethality caused by indomethacin.

The known compound 9-methyl-3-(5-tetrazolyl)-4-oxo-4-H-pyrido[ 1,2-a]pyrimidine potassium salt did not prevent the gastrointestinal ulceration induced by indomethacin.

The compounds of formulae (I) and (II) or their salts may therapeutically be used in the form of compositions containing the active ingredient in an admixture with inert solid or liquid organic or inorganic carriers. These compositions may be prepared by using methods well known in the pharmaceutical industry.

The compositions may be formulated for oral or parenteral use in the form of e.g. tablets, dragées,: capsules or in the sustained-release variants thereof. The compositions may contain suitable solid diluents or carriers, sterile aqueous solvents or non-toxic organic solvents. The compositions for oral use may be supplemented with sweetening or flavoring (aromatizing) agents which are suitable for this purpose.

Tablets for oral use may contain: carriers such as lactose, sodium citrate, or calcium carbonate; disintegrating agents such as starch or alginic acid; and sliding agents such as talc, sodium lauryl sulfate or magnesium stearate. The carrier in capsules may be e.g. lactose or polyethylene glycol. Aqueous suspensions may contain emulsifying or suspending agents. The diluent of a suspension in an organic solvent may be glycerol, ethanol, chloroform and the like.

The compositions for parenteral use are solutions or suspensions of the active ingredient in a suitable medium such as peanut oil, sesam oil, polypropylene glycol or water.

The active ingredient content of the pharmaceutical compositions according to the invention may be varied within wide limits: it may amount to 0.005 to 99%.

The daily dose of the active ingredient may also be varied within wide limits and depends on the severity of the disease as well as on the age and body weight of the patient, on the formulation of the composition and efficiency of the active ingredient used. For oral use, the daily dose of the active ingredient is commonly between 0.05 and 15 mg/kg daily once or in divided doses. However, the above data are only informative in character, which may be increased or lowered, dependently on the demands of the situation and prescriptions of the physician. When justified, compositions (formulations) differing from the above application forms may also be used.

The invention is illustrated in detail by the following non-limiting Examples.

EXAMPLE 1

Preparation of 3-(1-ethyl-1H-tetrazol-5-yl)-4-oxo-4H-pyrido[ (1,2-a]pyrimidine and 3-(2-ethyl-2H-tetrazol-5-yl)-4-oxo- 4H-pyrido[1,2-a]pyrimidine A mixture of 0.9 g (0.0042 moles) of 3-(1H-tetrazol-5-yl)- 4-oxo-4H-pyrido[1,2-a]pyrimidine, 25 ml of dimethylformamide, 0.58 g (0.0042 moles) of anhydrous potassium carbonate and 0.7 ml (0.0084 moles) of ethyl iodide were heated at 80°–90° C. under stirring for 3 hours. From the orange-colored solution the inorganic material was filtered off, and the filtrate was evaporated. To the residue 30 ml of water were added, and the crystals were separated. 0.4 g (40%) of the 1:1 isomeric mixture of the title compounds was obtained, m.p.: 160° C.

Analysis: Calculated for $C_{11}H_{10}N_6O$, C=54.54%; H=4.16%; N=34.70%;

Found: C=54.76%; H=4.40%; N=34.67%.

EXAMPLE 2

Preparation of 3- (1-methyl-1H-tetrazol-5-yl) -9-methyl-4-oxo- 4H-pyrido[1,2-a]pyrimidine and 3-(2-methyl-2H-tetrazol-5-yl)- 9-methyl-4-oxo-4H-pyrido-[1,2-a]pyrimidine A mixture of 0.4 g (0.0018 moles) of 3-(1H-tetrazol-5-yl)- 9-methyl-4-oxo-4H-pyrido[1,2-a]pyrimidine, 15 ml of dimethylformamide, 0.25 g (0.0018 moles) of anhydrous potassium carbonate and 0.51 ml (0. 0036 moles) of methyl iodide was stirred at 80° C. for 30 minutes. The yellow suspension gradually dissolved. From the warm yellow-colored solution the inorganic material was filtered off, and the filtrate was allowed to stay overnight in a refrigerator. The precipitated crystals were separated. 0.35 g (80.3%) isomeric mixture of the title compounds was obtained. The mixture was crystallized from dimethyl-formamide. 0.2 g (57%) of 3-(1-methyl- 1H-tetrazol-5-yl)-9-methyl-4-oxo-4H-pyrido[1,2-a] -pyrimidine was obtained in the form of white crystals, m.p.: 294° C. under decomposition.

Analysis: Calculated for $C_{11}H_{10}N_6O$ C=54.54%; H=4.16%; N=34.70%;

Found: C=54.27%; H=4.05%; N=34.36%.

EXAMPLE 3

Preparation of 3-(1-ethyl-1H-tetrazol-5-yl) -9-methyl-4-oxo- 4H-pyrido[1,2-a]pyrimidine and 3-(2-ethyl-2H-tetrazol- 5-yl)-9-methyl-4-oxo-4H-pyrido[1,2-a]pyrimidine A mixture of 0.55 g (0.0024 moles) of 3-(1H-tetrazol-5-yl)- 9-methyl-4-oxo-4H-pyrido[1,2-a]pyrimidine, 20 ml of dimethylformamide, 0.3 g (0.0024 moles) of anhydrous potassium carbonate and 0.4 ml (0.0048 moles) of ethyl iodide was stirred at 80° C. for 1 hour. The lemon-colored clear solution was filtered, and the filtrate was evaporated. To the yellow oily residue, which upon standing started to crystallize, 50 ml of ethanol were added, and the crystals were collected. 0.25 g (61.5%) of the 3:7 isomeric mixture of the title compounds was obtained, in the form of pale-yellow crystals. M.p.: 168°–170° C. (the ratio of the isomers was determined by $^1$Hnmr spectroscopy)

Analysis: Calculated for $C_{12}H_{12}N_6O$ C=54.54%; H=4.72%; N=32.80%;

Found: C=56.14%; H=4.80%; N=32.38%.

EXAMPLE 4

Preparation of 3-(1-propyl-1H-tetrazol-5-yl)-4-oxo-4H-pyrido[ 1,2-a]pyrimidine and 3-(2-propyl-2H-tetrazol-5-yl)- 4-oxo- 4H-pyrido[1,2-a]pyrimidine A mixture of 0.4 g (0.00187 moles) of 3-($^1$H-tetrazol-5-yl)- 4-oxo-4H-pyrido[1,2-a]pyrimidine, 15 ml of dimethylformamide, 0.25 g (0.00187 moles) of anhydrous potassium carbonate and 0.34 ml (0.00374 moles) of propyl bromide was stirred at 90° C. for 1 hour. The hot dark brown solution was filtered, and the filtrate was evaporated. The dark brown oily residue, which is the mixture of the title compounds, started to crystallize. To the oily crystals 10 ml of ethanol were added, and the crystals were collected. 0.15 g (31.3%) of 3-( 2-propyl-2H-tetrazol-5-yl)-4-oxo-4H-pyrido[1,2 -a]pyrimidine was obtained, in the form of pale-yellow crystals, m.p.: 115°–116° C.

Analysis: Calculated for $C_{12}H_{12}N_6O$ C=54.54%; H=4.72%; N=32.80%;

Found: C=56.21%; H=4.67%; N=32.75%.

EXAMPLE 5

Preparation of 3-(1-propyl-1H-tetrazol-5-yl)-9-methyl-4-oxo- 4H-pyrido[1,2-a]pyrimidine and 3-(2-propyl-2H-tetrazol-5-yl)- 9-methyl-4-oxo-4H-pyrido-[1,2-a]pyrimidine A mixture of 0.4 g (0.0018 moles) 3-($^1$H-tetrazol-5-yl)- 9-methyl-4-oxo-4H-pyrido[1,2-a]pyrimidine, 25 ml of dimethylformamide, 0.25 g (0.0018 moles) of anhydrous potassium carbonate and 0.33 ml (0.0036 moles) of propyl bromide was stirred at 90° C. for 1 hour. The yellow suspension gradually turned into a brown, clear solution which was filtered, and the filtrate was evaporated. To the brown, oily residue, 50 ml of cold ethanol were added, and the crystals were collected. 0.2 g (48.7%) 2:3 isomeric mixture of the title compounds was obtained, m.p.:

127°–128° C.

Analysis: Calculated for $C_{13}H_{14}N_6O$ C=57.77%; H=5.22%; N=31.09%;

Found: C=57.87%; H=5.32%; N=31.14%.

EXAMPLE 6

Preparation of 3-(1-methyl-1H-tetrazol-5-yl)-4-oxo-4H-pyrido[ 1,2-a]pyrimidine

A mixture of 4.28 g (0.02 moles) of 3-($^1$H-tetrazol-5-yl)-4-oxo-4H-pyrido[1,2-a]pyrimidine; 100 ml of dimethylformamide, 2.76 g (0.02 moles) of anhydrous potassium carbonate and 25 ml (0.04 moles) of methyl iodide was stirred at 75°–80° C. for 1 hour. The yellow suspension gradually dissolved and at the end of the reaction an orange-colored solution was obtained. The warm reaction mixture was filtered, cooled down and the precipitating crystals were collected. 2.3 g (50.4%) of the title compound were obtained, and crystallized from dimethylformamide to obtain white crystals, m.p.: 280°–282° C. (under decomposition).

Analysis: Calculated for $C_{10}H_8N_6O$ C=52.63%; H=3.53%; N=36.83%;

Found: C=52.56%; H=3.48%; N=36.89%.

EXAMPLE 7

Preparation of 3-(1-methyl-1H-tetrazol-5-yl) -4-oxo-4H-pyrido[ 1,2-a]pyrimidine and 3-(2-methyl-2H-tetrazol-5-yl)-4-oxo- 4H-pyrido [ 1,2-a ]pyrimidine The dimethylformamide mother liquor obtained in Example 6 was diluted with 50 ml of water, then extracted with 2× 50 ml of chloroform. The combined chloroformic phases were washed with 50 ml of water. The organic phase was dried on anhydrous sodium sulphate, filtered, and evaporated. To the crystalline residue cold ethanol was added, and the crystals were collected. 0.7 g (15.4%) of the 1:9 ratio mixture of the title compounds was obtained, m.p.: 208°–210° C. (the ratio of the isomers was determined by $^1$Hnmr spectroscopy)

Analysis: Calculated for $C_{10}H_8N_6O$ C=52.63%; H=3.53%; N=36.83%;

Found: C=52.75%; H=3.58%; N=36.69%.

EXAMPLE 8

Preparation of 3-(2-isopropyl-2H-tetrazol-5-yl)-4-oxo-4H-pyrido [1,2 -a ]pyrimidine A mixture of 0.9 g (0.0042 moles) of 3-($^1$H-tetrazol-5-yl)-4-oxo-4H-pyrido[1,2-a]pyrimidine, 25 ml of dimethylformamide, 1.15 g (0.0084 moles) of anhydrous potassium carbonate and 1.1 ml (0.0126 moles) of isopropyl bromide was stirred at 90° C. for 1 hour. The hot yellow solution was filtered, the filtrate evaporated. To the crystalline residue 25 ml of water was added, and the crystals were collected. 0.6 g (55.8%) of the title compound was obtained, in the form of white crystals, m.p.: 146°–148° C.

Analysis: Calculated for $C_{12}H_{12}N_6O$ C=56.24%; H=4.72%; N=32.80%;

Found: C=56.32%; H=4.81%; N=32.71%.

EXAMPLE 9

Preparation of 3-(1-isopropyl-1H-tetrazol-5-yl)-4-oxo- 4H-pyrido[ 1,2-a]pyrimidine and 3-(2-isopropyl-2H-tetrazol-5-yl)- 4-oxo-4H-pyrido[1,2-a]pyrimidine The aqueous mother liquor obtained in Example 8. was extracted with 2×20 ml of benzene. The combined organic phases were dried, filtered and evaporated. To the yellow crystalline residue 5 ml of cold ethanol were added, and the crystals were collected. 0.1 g (9.3%) of the 1:9 ratio mixture of the title compounds was obtained, m.p.: 135°–137° C. (the ratio of the isomers was determined by $^1$Hnmr spectroscopy).

Analysis: Calculated for $C_{12}H_{12}N_6O$ C=56.24%; H=4.72%; N=32.80%;

Found: C=56.39%; H=4.87%; N=32.67%.

EXAMPLE 10

Preparation of 3-(1-isopropyl-1H-tetrazol-5-yl)-9-methyl-4-oxo- 4H-pyrido[1,2-a]pyrimidine and 3-(2-isopropyl-2H-tetrazol- 5-yl)-9-methyl-4-oxo-4H-pyrido[1,2-a]-pyrimidine A mixture of 0.4 g (0.00175 moles) of 3-($^1$H-tetrazol-5-yl)- 9-methyl-4-oxo-4H-pyrido[1,2-a]pyrimidine, 15 ml of dimethylformamide, 0.25 g (0.0018 moles) of anhydrous potassium carbonate and 0.3 ml (0.0035 moles) of isopropyl bromide was stirred at 80° C. for 3 hours. The hot reaction mixture was filtered; the clear, yellow filtrate was cooled down and diluted with 10 ml of water, then extracted with 3×15 ml of benzene. The combined benzene phases were washed with 20 ml of water, dried on anhydrous sodium sulphate, filtered and evaporated. 0.2 g (42.0%) yellow crystals, of the 2:3 ratio mixture of the title compounds was obtained, m.p.: 143°–144° C.

Analysis: Calculated for $C_{13}H_{14}N_6O$ C=57.77%; H=5.22%; N=31.09%;

Found: C=57.85%; H=5.32%; N=31.13%.

EXAMPLE 11

Preparation of 3-(1-allyl-1H-tetrazol-5-yl)-4-oxo-4H-pyrido[ 1,2-a]pyrimidine and 3-(2-allyl-2H-tetrazol-5-yl)-4-oxo-4H-pyrido[ 1,2-a]-pyrimidine A mixture of 0.4 g (0.00187 moles) of 3-($^1$H-tetrazol-5-yl)- 4-oxo-4H-pyrido[1,2-a]pyrimidine, 15 ml of dimethylformamide, 0.25 g (0.0018 moles) of anhydrous potassium carbonate and 0.3 ml (0.0036 moles) of allyl bromide was stirred at 70° C. for 1 hour. The hot reaction mixture was filtered; the clear, orange-colored filtrate was evaporated; to the crystalline residue, 5 ml of ethanol were added. 0.1 g of white crystals were obtained which were the 1:1 ratio mixture of the title compounds, m.p.: 149°–151° C.

Analysis: Calculated for $C_{12}H_{10}N_6O$ C=56.68%; H=3.96%; N=33.05%;

Found: C=56.73%; H=4.04%; N=34.12%.

EXAMPLE 12

Preparation of 3-(1-allyl-1H-tetrazol-5-yl)-9-methyl-4-oxo 4H-pyrido[ 1,2-a]pyrimidine and 3- (2-allyl-2H-tetrazol-5-yl)- 9-methyl-4-oxo-4H-pyrido [1,2-a]pyrimidine A mixture of 0.4 g (0.00175 moles) of 3-($^1$H-tetrazol-5-yl)- 9-methyl-4-oxo-4H-pyrido[1,2-a]pyrimidine, 15 ml of dimethylformamide, 0.25 g (0.0018 moles) of anhydrous potassium carbonate and 0.31 ml (0.0036 moles) of allyl bromide was stirred at 70° C. for 1 hour. The hot reaction mixture was filtered; the filtrate was cooled down and diluted with 20 ml of water, then extracted with 3×15 ml of benzene. The combined benzene phases were dried on anhydrous sodium sulfate, filtered and evaporated. The yellow oily crystals were crystallized from ethanol to give 0.2 g (52.0%) of the 1:1 mixture of the title compounds, m.p.. 145°–150° C.

Analysis: Calculated for $C_{13}H_{12}N_6O$ C=58.20%; H=4.51%; N=31.33%;

Found: C=58.31%; H=4.59%; N=31.29%.

EXAMPLE 13

Preparation of 3-(1-methoxycarbonyl-1H-tetrazol-5-yl)-4-oxo- 4H-pyrido[1,2-a]pyrimidine and 3-(2-methoxycarbonyl-2H-tetrazol- 5-yl)-4-oxo-4H-pyrido[1,2-a]pyrimidine A mixture of 1.07 g (0.005 moles) of 3-($^1$H-tetrazol-5-yl)-4-oxo-4H-pyrido[1,2-a]pyrimidine; 45 ml of dimethylformamide, 0.75 g (0.0055 moles) of anhydrous potassium carbonate and 0.76 ml (0.01 moles) of methyl chloroformate was stirred at 80°–90° C. for 6 hours. The hot reaction mixture was filtered; the crystals precipitating from the filtrate were collected to obtain 0.32 g (23.5%) of the 1:1 ratio mixture of the title compounds, which on crystallization from ethanol gave the 3-(1-methoxycarbonyl-1H-tetrazol-5-yl)- 4-oxo-4H-pyrido[1,2-a]pyrimidine, m.p.: 182°–183° C.

Analysis: Calculated for $C_{11}H_8N_6O$ C=48.53%; H=2.96%; N=30.87%;

Found: C=48.61%; H=2.91%; N=30.92%.

EXAMPLE 14

Preparation of 3-(2-methoxycarbonyl-1H-tetrazol-5-yl)-9-methyl- 4-oxo-4H-pyrido[1,2-a]pyrimidine and 3-(2-methoxycarbonyl- 2H-tetrazol-5-yl)-9-methyl-4-oxo-4H-pyrido[1,2-a]pyrimidine A mixture of 0.25 g (0.0011 moles) of 3-($^1$H-tetrazol-5-yl)- 9-methyl-4-oxo-4H-pyrido[1,2-a]pyrimidine, 10 ml of dimethylformamide, 0.15 g (0.0011 moles) of anhydrous potassium carbonate and 0.17 ml (0.0022 moles) of methyl chloroformate was stirred at 80°–85° C. for 2 hours. The reaction mixture was diluted with 15 ml of water and extracted with 3 ×15 ml of benzene. The combined benzene phases were dried on anhydrous sodium sulfate, filtered and evaporated. 0.1 g (37.0%) crystals were obtained which were the mixture of the title compounds. The crystals were crystallized from ethanol to obtain yellow crystals of the 3-($^1$H-tetrazol-5-yl)-9-methyl- 4-oxo-4H-pyrido[1,2-a]a]pyrimidine isomer, m.p.: 240 ° C. (under decomposition).

Analysis: Calculated for $C_{12}H_{10}N_6O_3$ C=52.17%; H=3.65%; N=30.42%;

Found: C=52.21%; H=3.75%; N=30.28%.

EXAMPLE 15

Preparation of 3-[1-(3-methylbutyl)-1H-tetrazol-5-yl]-4-oxo 4H-pyrido[1,2-a]pyrimidine and 3-[2-(3-methyl-butyl)-2H-tetrazol- 5-yl]-4-oxo-4H-pyrido[1,2-a]pyrimidine A mixture of 1.07 g (0.005 moles) of 3-($^1$H-tetrazol-5-yl)-4-oxo-4H-pyrido[1,2-a]pyrimidine, 15 ml of dimethylformamide, 0.70 g (0.005 moles) of anhydrous potassium carbonate and 1.51 (0.01 moles) of 3-methylbutyl bromide was stirred at 100° C. for 3 hours. The hot reaction mixture was cooled down and diluted with 50 ml of water, then extracted with 3×25 ml of benzene. The combined benzene phases were dried on anhydrous sodium sulfate, filtered, and evaporated. 1.12 g (80.0%) oil, the isomeric mixture of the title compounds was obtained which crystallized upon standing at room temperature, m.p.: 90°–95° C.

Analysis: Calculated for $C_{14}H_{16}N_6O$ C=59.14%; H=5.67%; N=29.56%;

Found: C=59.30%; H=5.61%; N=29.67%.

EXAMPLE 16

Preparation of 3-(1-propargyl-1H-tetrazol-5-yl)-9-methyl-4-oxo- 4H-pyrido[1,2-a]pyrimidine and 3-(2-propargyl-2H-tetrazol- 5-yl)-9-methyl-4-oxo-4H-pyrido[1,2-a]-pyrimidine A mixture of 3.42 g (0.015 moles) of 3-($^1$H-tetrazol-5-yl)-9-methyl-4-oxo-4H-pyrido[1,2-a]pyrimidine, 35 ml of dimethylformamide, 2.07 g (0.015 moles) of anhydrous potassium carbonate and 3.57 ml (0.03 moles) of propargyl bromide was stirred at 100° C. for 10 hour. The reaction mixture was cooled down and diluted with 100 ml of water. The resulting crystals were collected, and washed with water. 2.46 g (61.65%) of an isomeric mixture of the title compounds were obtained, m.p.: 182°–184° C.

Analysis: Calculated for $C_{13}H_{10}N_6O$ C=58.64%; H=3.79%; N=31.56%;

Found: C=58.52%; H=3.64%; N=31.82%.

EXAMPLE 17

Preparation of 3-(1-p-chlorobenzyl-1H-tetrazol-5-yl)-4-oxo- 4H-pyrido[1,2-a]pyrimidine and 3-(2-p-chloro-benzyl-2H-tetrazol- 5-yl)-4-oxo-4H-pyrido[1,2-a]-pyrimidine A mixture of 4.28 g (0.02 moles) of 3-($^1$H-tetrazol-5-yl)-4-oxo-4H-pyrido[1,2-a]pyrimidine, 50 ml of dimethyl-formamide, 2.76 g (0.02 moles) of anhydrous potassium carbonate and 6.0 g (0.04 moles) of p-chlorobenzyl chloride was stirred at 100° C. for 3 hours. The reaction mixture was cooled down and diluted with 100 ml of water. The precipitating yellow crystals were collected, washed with water to obtain 4.27 g (63.73%) of the 1:1 mixture of the title compounds; m.p.: 166°–167° C.

Analysis: Calculated for $C_{16}H_{11}N_6OCl$ C=56.73%; H=3.27%; N=24.81%; Cl=10.47;

Found: C=56.89%; H=3.45%; N=24.79%; Cl=10.28.

EXAMPLE 18

Preparation of 3-(1-isoamyl-1H-tetrazol-5-yl)-9-methyl-4-oxo- 4H-pyrido[1,2-a]pyrimidine and 3-(2-isoamyl-2H-tetrazol- 5-yl)-9-methyl-4-oxo-4H-pyrido-[1,2-a]pyrimidine A mixture of 3.42 g (0.015 moles) of 3-($^1$H-tetrazol-5-yl)-9-methyl-4-oxo-4H-pyrido[1,2-a]pyrimidine, 30 ml of dimethylformamide, 2.07 g (0.015 moles) of anhydrous potassium carbonate and 4.53 ml (0.03 moles) of isoamyl bromide was stirred at 100° C. for 3 hours. The reaction mixture was diluted with 100 ml of water. The precipitating brown oil crystallized upon standing. The crystals were collected, and washed with water. 2.65 g (59.20%) of a mixture of the title compounds were obtained, m.p.: 124°–126° C.

Analysis: Calculated for $C_{15}H_{16}N_6O$ C=60.39%; H=6.08%; N=28.17%;

Found: C=60.08%; H=6.26%; N=28.35%.

EXAMPLE 19

Preparation of 3- (1-phenylethyl-1H-tetrazol-5-yl)-9-methyl- 4-oxo-4H-pyrido[1,2-a]pyrimidine and 3-(2-phenylethyl-2H-tetrazol- 5-yl)-9-methyl-4-oxo-4H-pyrido[1,2-a] pyrimidine A mixture of 4.56 g (0.02 moles) of 3-(¹H-tetrazol-5-yl)-9-methyl-4-oxo-4H-pyrido[1,2-a]pyrimidine, 60 ml of dimethylformamide, 2.8 g (0.02 moles) of anhydrous potassium carbonate and 7.4 g (0.04 moles) of 2-phenylethyl bromide was stirred at 100° C. for 3 hours. The yellow suspension was poured onto 180 ml of water. The precipitating crystals were collected, washed with water, to obtain 5.84 g (87.82%) of the 3:7 mixture of the title compounds, m.p.: 153°–155° C.

Analysis: Calculated for $C_{16}H_{16}N_6O$ C=65.05%; H=4.85%; N=25.29%;

Found: C=65.38%; H=4.89%; N=25.44%.

EXAMPLE 20

Preparation of 3-(1-isobutyl-1H-tetrazol-5-yl)-9-methyl-4-oxo-4H-pyrido[1,2-a]pyrimidine and 3-(2-isobutyl-2H-tetrazol-5-yl)-9-methyl-4-oxo-4H-pyrido[1,2-a]pyrimidine A mixture of 9.13 g (0.04 moles) of 3-(¹H-tetrazol-5-yl)-9-methyl-4-oxo-4H-pyrido[1,2-a]pyrimidine, 100 ml of dimethylformamide; 5.53 g (0.04 moles) of anhydrous potassium carbonate and 11.0 g (0.08 moles) of isobutyl bromide was stirred at 100° C. for 5 hours. The reaction mixture was diluted with 300 ml of water. The precipitating oil crystallized upon longer standing and cooling. The crystals were collected, washed with water. 8.28 g (73.34%) of the 3:7 isomeric mixture of the title compounds were obtained, m.p.: 108°–109° C.

Analysis: Calculated for $C_{14}H_{16}N_6O$ C=59.57%; H=5.71%; N=29.77%;

Found: C=59.87%; H=5.63%; N=29.52%.

EXAMPLE 21

Preparation of 3-(2-propyl-2H-tetrazol-5-yl)-9-methyl-4-oxo-4H-pyrido[1,2-a]pyrimidine hydrochloride salt 1.5 g (0.0055 moles) of 3-(2-propyl-2H-tetrazol-5-yl)-9-methyl-4-oxo-4H-pyrido[1,2-a]pyrimidine was dissolved in 20 ml of abs. ethanol under heating and stirring. To the solution 10 ml of 10% aqueous hydrochloric acid solution was added dropwise. After a few minutes of stirring the mixture was filtered and the filtrate was cooled down. The precipitating crystals were collected, 1.50 g (89.29%) of the title compound were obtained in the form of white crystals, m.p.: 198°–199° C.

Analysis: Calculated for $C_{13}H_{15}ClN_6O$ C=50.90%; H=4.93%; N=27.40%; Cl=11.56%;

Found: C=50.87%; H=4.87%; N=27.18%; Cl=11.50%.

EXAMPLE 22

Preparation of 3-(2-propyl-2H-tetrazol-5-yl)-9-methyl-4-oxo-4H-pyrido[1,2-a]pyrimidine methane-sulfonic acid salt 1.5 g (0.0055 moles) of 3-(2-propyl-2H-tetrazol-5-yl)-9-methyl-4-oxo-4H-pyrido[1,2-a]pyrimidine was dissolved in 20 ml of abs. ethanol under heating and stirring at reflux temperature. To the solution 0.6 ml (0.009 moles) of methanesulfonic acid was added dropwise. After a few minutes of stirring the reaction mixture was filtered and the filtrate was cooled down. The precipitating crystals were collected. 1.77 g (87.84%) of the title compound were obtained in the form of white crystals, m.p.: 154°–155° C.

Analysis: Calculated for $C_{14}H_{18}N_6O_4S$ C=45.89%; H=4.95%; N=22.94%; S=8.75%;

Found: C=45.73%; H=4.91%; N=22.72%; S=8.96%.

EXAMPLE 23

Hydrochloric acid addition salt of the 3-(2-isopropyl-2H-tetrazol-5-yl)-4-oxo-4H-pyrido[1,2-a]pyrimidine prepared similarly as described in Example 22, is a white crystalline material, m.p.: 222° C. (under decomposition).

Analysis: Calculated for $C_{12}H_{13}ClN_6O$ C=49.24%; H=4.48%; N=28.71%; Cl=12.11%;

Found: C=49.42%; H=4.18%; N=28.48%; Cl=12.23%.

EXAMPLE 24

Hydrochloric acid addition salt of the 3-(2-isopropyl-2H-tetrazol-5-yl)-9-methyl-4-oxo-4H-pyrido[1,2-a]pyrimidine prepared similarly aa described in Example 22, is a white crystalline material, m.p.: 219° C. (under decomposition).

Analysis: Calculated for $C_{13}H_{15}ClN_6O$ C=50.90%; H=4.93%; N=27.40%; Cl=11.56%;

Found: C=50.99%; H=4.90%; N=26.97%; Cl=11.49.

EXAMPLE 25

Methanesulfonic acid addition salt of the 3-(2-iso-propyl-2H-tetrazol-5-yl)-4-oxo-4H-pyrido[1,2-a]pyrimidine prepared similarly as described in Example 23, is a white crystalline material, m.p.: 213°–214° C.

Analysis: Calculated for $C_{13}H_{16}N_6O_4S$

C=44.31%; H=4.58%; N=23.85%; Cl=9.10

Found: C=44.22%; H=4.33%; N=23.52%; Cl=9.28.

EXAMPLE 26

Methanesulfonic acid addition salt of the 3-(2-isopropyl-2H-tetrazol-5-yl)-9-methyl-4-oxo-4H-pyrido-[1,2-a]pyrimidine prepared similarly as described in Example 23, is a white crystalline material, m.p.: 155°–156° C.

Analysis: Calculated for $C_{14}H_{18}N_6O_4S$

C=45.89%; H=4.95%; N=22.94%; S=8.75;

Found: C=45.70%; H=4.75%; N=22.40%; S=8.74.

EXAMPLE 27

Hydrochloric acid addition salt of the 3-(2-allyl-2H-tetrazol-5-yl)-9-methyl-4-oxo-4H-pyrido[1,2-a]pyrimidine prepared similarly as described in Example 22, is a white crystalline material, m.p.: 203° C. (under decomposition).

Analysis: Calculated for $C_{13}H_{13}C_1N_6O$

C=51.24%; H=4.30%; N=27.58%; Cl=11.63;

Found: C=51.06%; H=3.99%; N=27.28%; Cl=11.97.

EXAMPLE 28

Methanesulfonic acid addition salt of the 3-(2-allyl-2H-tetrazol-5-yl)-9-methyl-4-oxo-4H-pyrido[1,2-a]pyrimidine prepared similarly as described in Example 23, is a white crystalline material, m.p.: 156°–157° C.

Analysis: Calculated for $C_{14}H_{16}N_6O_4S$ C=46.15%; H=4.43%; N=23.06%; S=8.80;

Found: C=45.91%; H=4.47%; N=23.48%; S=8.54.

EXAMPLE 29

Preparation of 3-(1-methyl-1H-tetrazol-5-yl)-6-methyl-4-oxo-4H-pyrido[1,2-a]pyrimidine A mixture of 2.3 g of 3-(¹H-tetrazol-5-yl)-6-methyl-4-oxo-4H-pyrido[1,2-a]pyrimidine, 50 ml of dimethylformamide, 1.38 g (0.001 mole) of anhydrous potassium carbonate and 2.85 g (0.02 moles) of methyl iodide was stirred at 80° C. for 1 hour. The reaction mixture was cooled to room temperature and diluted with 150 ml of water. The precipitating crystals were collected. 1.61 g (66.53%) of the title compound was obtained, which was crystallized from dimethylformamide, m.p.: 232°–234° C.

Analysis: Calculated for $C_{11}H_{10}N_6O$ C=54.54%; H=4.16%; N=34.69%;

Found: C=54.83%; H=3.76%; N=34.92%.

EXAMPLE 30

Preparation of 3-(1-butyl-1H-tetrazol-5-yl) -4-oxo-4H-pyrido[ 1,2-a]pyrimidine and 3-(2-butyl-2H-tetrazol-5-yl) -4-oxo-4H-pyrido[ 1,2-a]pyrimidine A mixture of 4.8 g (0.0224 moles) of 3-($^1$H-tetrazol-5-yl)-4-oxo-4H-pyrido[1,2-a]pyrimidine, 100 ml of dimethylformamide, 3.2 g (0.0232 moles) of anhydrous potassium carbonate and 6.13 g (0. 0448 moles) of butyl bromide was stirred at 80°–85° C. for 3 hours. The reaction mixture was cooled down to room temperature, diluted with 300 ml of water, and extracted with 3×25 ml of benzene. The combined benzene phases were dried on anhydrous sodium sulfate, filtered and evaporated. 4.77 g (78.84%) oil, the isomeric mixture of the title compounds was obtained which crystallized upon staying at room temperature, m.p.: 98°–100° C.

Analysis: Calculated for $C_{13}H_{14}N_6O$ C=57.77%; H=5.22%; N=31.09%;

Found: C=58.11%; H=5.22%; N=31.33%.

EXAMPLE 31

Preparation of 3-(1-isobutyl-1H-tetrazol-5-yl)-4-oxo-4H-pyrido[ 1,2-a]pyrimidine and 3-(2-iso-butyl-2H-tetrazol-5-yl)- 4-oxo-4H-pyrido[1,2-a]-pyrimidine A mixture of 1.07 g (0.005 moles) of 3-($^1$H-tetrazol-5-yl)-4-oxo-4H-pyrido[1,2-a]pyrimidine, 15 ml of dimethylformamide, 0.70 g (0.005 moles) of anhydrous potassium carbonate and 1.32 g (0.01 mole) of isobutyl bromide was stirred at 100° C. for 5 hours. The reaction mixture was cooled down to room temperature and diluted with 50 ml of water, then extracted with 3×25 ml of benzene. The combined benzene phases were dried on anhydrous sodium sulfate, filtered and evaporated. 1.03 g (76.3%) oil, the isomeric mixture of the title compounds was obtained which crystallized upon staying at room temperature, m.p.. 85°–89° C.

Analysis: Calculated for $C_{13}H_{14}N_6O$ C=57.77%; H=5.22%; N=31.09%;

Found: C=57.52%; H=5.08%; N=31.25%.

EXAMPLE 32

Preparation of 3-(1-ethyl-1H-tetrazol-5-yl) -6-methyl-4-oxo- 4H-pyrido([1,2-a]pyrimidine and 3-(2-ethyl-2H-tetrazol-5-yl)- 6-methyl-4-oxo-4H-pyrido-[1,2-a]pyrimidine A mixture of 2.3 g (0.01 mole) of 3-($^1$H-tetrazol-5-yl)- 6-methyl-4-oxo-4H-pyrido[1,2-a]pyrimidine, 50 ml of dimethylformamide, 1.38 g (0.01 mole) of anhydrous potassium carbonate and 3.12 g (0.02 moles) of ethyl iodide was stirred at 80° C. for 1 hour. The hot reaction mixture was diluted with 150 ml of water. After longer staying and cooling a crystalline material precipitated, the crystals were collected, washed with water. 0.63 g (24.6%) of the isomeric mixture of the title compounds was obtained: m.p.: 182°–184 ° C.

Analysis: Calculated for $C_{12}H_{12}N_6O$ C=56.24%; H=4.72%; N=32.79%;

Found: C=56.52%; H=4.81%; N=32.72%.

EXAMPLE 33

Preparation of 3-(1-ethyl-1H-tetrazol-5-yl) -6-methyl-4-oxo- 4H-pyrido[1,2-a]pyrimidine and 3-(2-ethyl-2H-tetrazol-5-yl)- 6-methyl-4-oxo-4H-pyrido[1,2-a]-pyrimidine A mixture of 2.3 g (0.01 mole) of 3-($^1$H-tetrazol-5-yl)-6-methyl-4-oxo-4H-pyrido[1,2-a]pyrimidine, 8.5 ml (0.05 moles) of triethyl phosphate and 1.38 g (0.01 mole) of anhydrous potassium carbonate was stirred at 280° C. for 30 minutes. The hot reaction mixture was diluted with 150 ml of water, cooled down and extracted with 3×30 ml of benzene. The combined benzene phases were decolorized on charcoal, dried on anhydrous sodium sulfate, filtered, and evaporated. To the oily residue 20 ml of diethyl ether was added, the crystalline product was collected. 1.12 g (80.0%) crystals were obtained, which were the 1:4 isomeric mixture of the title compounds, m.p.: 122°–130° C.

Analysis: Calculated for $C_{12}H_{12}N_6O$ C=56.24%; H=4.72%; N=32.79%;

Found: C=56.11%; H=4.58%; N=32.87%.

EXAMPLE 34

Preparation of 3-(1-cyclopentyl-1H-tetrazol-5-yl)-9-methyl- 4-oxo-4H-pyrido[1,2-a]pyrimidine and 3-(2-cyclopentyl-2H-tetrazol- 5-yl)-9-methyl-4-oxo-4H-pyrido[1,2-a]pyrimidine A mixture of 6.85 g (0.03 moles) of 3-($^1$H-tetrazol-5-yl)-9-methyl-4-oxo-4H-pyrido[1,2-a]pyrimidine, 35 ml of dimethylformamide, 4.17 g (0.03 moles) of anhydrous potassium carbonate and 8.94 g of cyclopentyl bromide was stirred at 100° C. for 5 hours. The reaction mixture was cooled down to room temperature and it was poured onto 450 ml of cold water. The resulting crystals were collected, washed with water. 7.08 g (79.64%) of the 1:4 isomeric mixture of the title compounds were obtained, m.p.: 130°–131° C. (The isomeric ratio was determined on the basis of the $^1$Hnmr spectrum)

Analysis: Calculated for $C_{15}H_{16}N_6O$ C=60.80%; H=5.44%; N=28.36%;

Found: C=60.21%; H=5.36%; N=28.36%.

EXAMPLE 35

Preparation of 3-(1-p-nitrobenzyl-1H-tetrazol-5-yl)-6-methyl- 4-oxo-4H-pyrido[1,2-a]pyrimidine and 3-(2-p-nitrobenzyl- 2H-tetrazol-5-yl)-6-methyl-4-oxo-4H-pyrido[1, 2-a]pyrimidine A mixture of 2.28 g (0.01 mole) of 3-($^1$H-tetrazol-5-yl)-6-methyl-4-oxo-4H-pyrido[1,2-a]pyrimidine, 50 ml of dimethylformamide, 1.38 g (0.01 mole) of anhydrous potassium carbonate and 3.43 g (0.02 moles) of p-nitrobenzyl chloride was stirred at 100° C. for 3 hours. The reaction mixture was cooled down to room temperature and diluted with 150 ml of water. The crystals, precipitating after a long standing, were collected. 2.26 g (62.26%) of the 3:2 isomeric mixture of the title compounds were obtained; m.p.: 182°–184° C. (under decomposition).

Analysis: Calculated for $C_{17}H_{13}N_7O_3$ C=56.20%; H=3.61%; N=26.98%;

Found: C=56.43 %; H=3.94%; N=26.46%.

EXAMPLE 36

Formulation

Composition of tablets containing 100 mg active ingredient:

| | |
|---|---|
| 3-(2-propyl-2H-tetrazol-5-yl)-9-methyl-4-oxo-4H-pyrido[1,2-a]pyrimidine | 10.0 g |
| CMC-Na | 2.0 g |
| Lactose | 1.5 g |
| Plaster | 12.0 g |
| Stearic acid | 1.5 g |
| Magnesium stearate | 0.25 g |
| Talc | 0.5 g |

EXAMPLE 37

Preparation of 3-(2-propyl-2H-tetrazol-5-yl)-6-methyl-4-oxo- 4H-pyrido[1,2-a]pyrimidine A mixture of 3.62 g (0.0159 moles) of 3-($^1$H-tetrazol-5-yl)- 6-methyl-4-oxo-4H-pyrido[1,2-a]pyrimidine, 30 ml of dimethyl formamide, 2.21 g (0.016 moles) of anhydrous potassium carbonate and 3.70 g (0.03 moles) of propyl bromide is stirred at a temperature of 100° C. for one hour.

The reaction mixture is diluted with 60 ml of water while hot, cooled and shaken three times with 35 ml of benzene each. The combined benzene phase is dried over anhydrous sodium sulfate, filtered and evaporated.

The oily residue is separated by column chromatography (column: Kieselgel 60, eluent: chloroform and methanol). 2.12 g (57.30%) of the title compound are obtained by recrystallizing from diisopropyl ether in the form of a bright yellow crystalline substance which melts at 88°–90° C.

Analysis: Calculated for $C_{13}H_{14}N_6O$ C=57.77%; H=5.22%; N=31.09%;

Found: C=57.83%; H=5.10%; N=30.78%.

EXAMPLE 38

Preparation of 3-(1-propyl-1H-tetrazol-5-yl)-6-methyl-4-oxo-pyrido[ 1,2-a]pyrimidine During the column chromatography separation process described in Example 37 1.20 g (32.43%) of 3-(1-propyl-1H-tetrazol- 5-yl)-6-methyl-4-oxo-pyrido[1,2-a]pyrimidine are obtained in the form of a crystalline product which melts at 137° C.

Analysis: Calculated for $C_{13}H_{14}N_6O$ C=57.77%; H=5.22%; N=31.09%;

Found: C=57.53%; H=4.81%; N=30.65%.

EXAMPLE 39

Preparation of 3-(2-isopropyl-2H-tetrazol-5-yl)-6-methyl- 4-oxo-4H-pyrido[1,2-a]pyrimidine A mixture of 4.60 g (0.0200 moles) of 3-($^1$H-tetrazol-5-yl)- 6-methyl-4-oxo-4H-pyrido[1,2-a]pyrimidine, 100 ml of dimethyl formamide, 2.76 g (0.020 moles) of anhydrous potassium carbonate and 4.92 g (0.04 moles) of isopropyl bromide is stirred at a temperature of 100° C. for 2 hours.

The reaction mixture is diluted with 200 ml of water while hot, cooled and shaken three times with 60 ml of benzene each. The combined benzene phase is dried over anhydrous sodium sulfate, filtered and evaporated.

The oily residue is separated by column chromatography (column: Kieselgel 60, eluent: chloroform and methanol). 3.34 g (71.83%) of the title compound are obtained by recrystallizing from abs. ethanol in the form of a yellow crystalline substance which melts at 117°–118°° C.

Analysis: Calculated for $C_{13}H_{14}N_6O$ C=57.77%; H=5.22%; N=31.09%;

Found: C=57.66%; H=5.28%; N=30.85%.

EXAMPLE 40

Preparation 3-(1-isopropyl-1H-tetrazol-5-yl)-6-methyl-4-oxo-pyrido[ 1,2-a]pyrimidine During the column chromatography separation process described in Example 39 1.19 g (25.60%) of the title compound are obtained in the form of a crystalline product which melts at 166°–167° C.

Analysis: Calculated for $C_{13}H_{14}N_6O$ C=57.77%; H=5.22%; N=31.09%;

Found: C=57.84%; H=5.27%; N=31.51%.

EXAMPLE 41

Preparation of 3-(2-pentyl-2H-tetrazol-5-yl)-6-methyl-4-oxo- 4H-pyrido[1,2-a]pyrimidine A mixture of 2.28 g (0.0100 mole) of 3-($^1$H-tetrazol-5-yl)-6-methyl-4-oxo-4H-pyrido[1,2-a]pyrimidine, 25 ml of dimethyl formamide, 1.38 g (0.010 mole) of anhydrous potassium carbonate and 3.02 g (0.02 moles) of pentyl bromide is stirred at a temperature of 100°–110° C. for 1 hour.

The reaction mixture is diluted with 75 ml of water while hot, cooled under stirring and shaken three times with 60 ml of benzene each. The combined benzene phases are dried over anhydrous sodium sulfate, filtered and evaporated.

The oily residue is separated by column chromatography (column: Kieselgel 60, eluent: chloroform and methanol). 1.20 g (44.28%) of the title compound are obtained which is a yellowish brown oil at room temperature.

Analysis: Calculated for $C_{15}H_{18}N_6O$ C=60.39%; H=6.08%; N=28.17%;

Found: C=60.74%; H=6.12%; N=28.37%.

EXAMPLE 42

Preparation of 3-(1-pentyl-1H-tetrazol-5-yl)-6-methyl-4-oxo-pyrido[ 1,2-a]pyrimidine During the column chromatography separation process described in Example 41, 0.71 g (26.20%) of the title compound are obtained in the form of a crystalline product which melts at 113°–115° C.

Analysis: Calculated for $C_{15}H_{18}N_6O$ C=60.39%; H=6.08%; N=28.17%;

Found: C=61.12%; H=6.17%; N=28.08%.

EXAMPLE 43

Preparation of 3-(1-ethoxycarbonyl-methyl-1H-tetrazol-5-yl)- 6-methyl-4-oxo-4H-pyrido[1,2-a]pyrimidine and 3-(2-ethoxycarbonyl-methyl- 2H-tetrazol-5-yl)-4-oxo-4H-pyrido[1,2-a]pyrimidine A mixture of 2.28 g (0.0100 mole) of 3-($^1$H-tetrazol-5-yl)-6-methyl-4-oxo-4H-pyrido[1,2-a]pyrimidine, 25 ml of dimethyl formamide, 1.38 g (0.010 mole) of anhydrous potassium carbonate and 5.01 g (0.03 moles) of bromoacetic ethyl ester is stirred at a temperature of 100° C. for 1 hour.

The reaction mixture is diluted with 75 ml of water while hot. The crystalline substance precipitated during cooling is separated by suction in vacuo.

2.00 g (63.70%) of a 96: 4 isomeric mixture of the title compounds are obtained in the form of a crystalline substance which melts at 164°–165° C.

Analysis: Calculated for $C_{14}H_{14}N_6O_3$ C=53.50%; H=4.49%; N=26.74%;

Found: C=53.39%; H=4.54%; N=26.31%.

EXAMPLE 44

Preparation of 3-[1-(4-bromobenzyl)-$^1$H-tetrazol-5-yl]-9-methyl-4-oxo- 4H-pyrido[1,2-a]pyrimidine and 3-[2-(4-bromobenzyl)-2H-tetrazol- 5-yl)-9-methyl-4-oxo-4H-pyrido [1,2 -a]pyrimidine A mixture of 2.28 g (0.0100 mole) of 3-($^1$H-tetrazol-5-yl)-9-methyl-4-oxo-4H-pyrido[1,2-a]pyrimidine, 50 ml of dimethyl formamide, 1.38 g (0.010 mole) of anhydrous potassium carbonate and 2.49 g (0.01 mole) of 4-bromobenzyl bromide is stirred at a temperature of 100° C. for 3 hours.

The reaction mixture is diluted with 100 ml of water while hot. The crystalline substance precipitated during cooling is separated by suction in vacuo.

3.06 g (77.08%) of a 59:41 mixture of 3-[1-(4-bromobenzyl)- 1H-tetrazol-5-yl] and 3-[2-(4-bromobenzyl)-2H-tetrazol- 5-yl)-9-methyl-4-oxo-4H-pyrido[1,2-a]pyrimidine isomers are obtained in the form of a crystalline substance which melts at 166°–170° C.

Analysis: Calculated for $C_{17}H_{13}BrN_6O$ C=51.40%; H=3.30%; N=26.16%; Br=20.12%;

Found: C=51.81%; H=3.35%; N=21.60%. Br=19.50%.

EXAMPLE 45

Preparation of 3-[1-(3,4-dichlorobenzyl)-1H-tetrazol-5-yl)- 9-methyl-4-oxo-4H-pyrido[1,2-a]pyrimidine and 3-[2-(3,4-dichlorobenzyl)- 2H-tetrazol-5-yl)-9-methyl-4-oxo-4H-pyrido[1,2-a]pyrimidine A mixture of 2.28 g (0.0100 mole) of 3-(1H-tetrazol-5-yl)- 9-methyl-4-oxo-4H-pyrido[1,2-a]pyrimidine, 30 ml of dimethyl formamide, 1.38 g (0.010 mole) of anhydrous potassium carbonate and 1.95 g (0.02 moles) of 3,4-dichlorobenzyl chloride is stirred at a temperature of 100° C. for 3 hours.

The reaction mixture is diluted with 100 ml of water while hot. The crystalline substance precipitated is separated by suction in vacuo after cooling.

3.35 g (86.56%) of a 2:1 isomeric mixture of the title compounds are obtained in the form of a crystalline substance which melts at 168°–170° C.

Analysis: Calculated for $C_{17}H_{12}Cl_2N_6O$ C=52.73%; H=3.12%; N=21.70%; Cl=18.31%;

Found: C=52.20%; H=2.94%; N=20.99%. Cl=18.56.

We claim:
1. A compound of the formula

$$（I）$$

wherein
R is a $C_{1-6}$alkyl, $C_{3-6}$alkenyl, $C_{3-6}$alkynyl, $C_{3-7}$cycloalkyl, —$(CH_2)_n$—$COOR^3$ wherein $R^3$ is $C_1$ to $C_4$ alkyl and n is 0 or 1 or a $C_{7-8}$ aralkyl group, unsubstituted or substituted by at least one halogen atom, or by a nitro-group and $R^1$ is a hydrogen atom or a $C_{1-4}$ alkyl group, or a pharmaceutically acceptable salt thereof.

2. A compound of the formula $$（II）$$

wherein
R is a $C_{1-6}$alkyl, $C_{3-6}$alkenyl, $C_{3-6}$alkynyl, $C_{3-7}$cycloalkyl, —$(CH_2)_n$—$COOR^3$ wherein $R^3$ is $C_1$ to $C_4$ alkyl and n is 0 or 1 or a $C_{7-8}$ aralkyl group, unsubstituted or substituted by at least one halogen atom, or by a nitro-group and $R^1$ is a hydrogen atom or a $C_{1-4}$ alkyl group or a pharmaceutically acceptable salt thereof.

3. 3-(2-allyl-2H-tetrazol-5-yl)-9-methyl-4-oxo-4-H-pyrido[ 1,2-a]pyrimidine or a pharmaceutically acceptable salt thereof.

4. 3-(2-propyl-2H-tetrazol-5-yl)-9-methyl-4-oxo-4-H-pyrido[ 1,2-a]pyrimidine or a pharmaceutically acceptable salt thereof as defined in claim 2.

5. 3-(2-isopropyl-2H-tetrazol-5-yl)-9-methyl-4-oxo-4H-pyrido[1,2-a]pyrimidine or a pharmaceutically acceptable salt thereof defined in claim 2.

6. 3-(2-isopropyl-2H-tetrazol-5-yl)-4-oxo-4-H-pyrido[ 1,2-a]pyrimidine or a pharmaceutically acceptable salt thereof defined in claim 2.

7. 3-(1-isopropyl-1H-tetrazol-5-yl)-9-methyl-4-oxo-4H-pyrido[1,2-a]pyrimidine or a pharmaceutically acceptable salt thereof defined in claim 1.

8. A pharmaceutical composition for the prevention of a gastric ulcer which comprises a therapeutically effective amount of a compound of the Formula (I) as defined in claim 1 or a pharmaceutically acceptable salt thereof, in admixture with a pharmaceutically acceptable inert carrier.

9. A pharmaceutical composition for the prevention of a gastric ulcer which comprises a therapeutically effective amount of a compound of the Formula (II) as defined in claim 2 or a pharmaceutically acceptable salt thereof, in admixture with a pharmaceutically acceptable inert carrier.

10. A method of preventing occurrence of a gastric ulcer or of promoting healing of a gastric ulcer in a mammalian subject which comprises the step of administering to said mammalian subject, a therapeutically effective amount of the compound of the Formula (I) defined in claim 1 or a pharmaceutically acceptable salt thereof.

11. A method of preventing occurrence of a gastric ulcer or of promoting healing of a gastric ulcer in a mammalian subject which comprises the step of administering to said mammalian subject, a therapeutically effective amount of the compound of the Formula (II) defined in claim 2 or a pharmaceutically acceptable salt thereof.

* * * * *